United States Patent [19]

Hardtmann

[11] B 3,997,555

[45] Dec. 14, 1976

[54] 4-PHENYL-1-HYDROXYALKYL-PYRAZOLES

[75] Inventor: Goetz E. Hardtmann, Florham Park, N.J.

[73] Assignee: Sandoz, Inc., E. Hanover, N.J.

[22] Filed: Dec. 23, 1974

[21] Appl. No.: 535,437

[44] Published under the second Trial Voluntary Protest Program on February 24, 1976 as document No. B 535,437.

[52] U.S. Cl. .......................... 260/310 R; 424/273
[51] Int. Cl.² .............. C07D 231/12; A61K 31/415
[58] Field of Search ................. 260/310 R

[56] References Cited

UNITED STATES PATENTS

| | | | |
|---|---|---|---|
| 2,883,392 | 4/1959 | Karmas et al. | 260/310 R |
| 3,043,819 | 7/1962 | Lynn | 260/310 R |

FOREIGN PATENTS OR APPLICATIONS

| | | | |
|---|---|---|---|
| 1,364,310 | 7/1963 | France | 260/310 R |

Primary Examiner—Donald B. Moyer
Attorney, Agent, or Firm—Gerald D. Sharkin; Richard E. Vila

[57] ABSTRACT

CNS depressants of the formula:

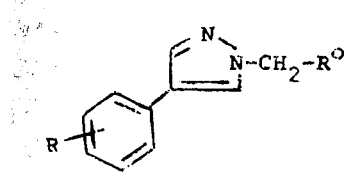

wherein R° is hydroxyalkyl of 1 to 5 carbon atoms and R is hydrogen, halo, alkyl, alkoxy or trifluoromethyl.

10 Claims, No Drawings

4-PHENYL-1-HYDROXYALKYLPYRAZOLES

The present invention relates to chemical compounds which are 4-phenyl-1-hydroxyalkylpyrazoles, and to their preparation. The invention also relates to pharmaceutical methods and compositions for utilizing the compounds based on their pharmacological activity, and in particular their CNS depressant activity.

The compounds of the present invention may be represented by the structural formula I:

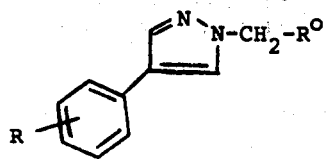

wherein
$R^o$ is hydroxyalkyl of 1 to 5 carbon atoms, and
R is hydrogen, halo of atomic weight of from 18 to 80, i.e., fluoro, chloro or bromo, alkyl of 1 to 4 carbon atoms, alkoxy of 1 to 4 carbon atoms or trifluoromethyl,
or a pharmaceutically acceptable acid addition salt thereof.

The alkyl portion of the $R^o$ hydroxyalkyl substituent may be straight chain or branched. Such alkyl portion is preferably straight chain and more preferably of the formula A:

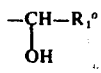

wherein $R_1^o$ is straight chain alkyl of 1 to 4 carbon atoms. The particularly preferred $R^o$ substituent is of the formula B:

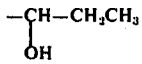

The compounds of the formula I may be prepared by reacting a compound of the formula II:

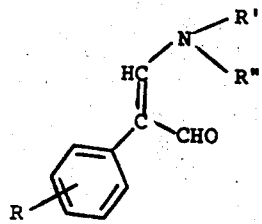

wherein R is as above defined, R' is alkyl of 1 to 4 carbon atoms and R" is alkyl of 1 to 4 carbon atoms or phenyl, with a compound of the formula III:
wherein $R^o$ is as above defined.

The preparation of compound I by the reaction of a compound II with a compound III is suitably carried out in an inert organic solvent at temperatures in the range of from 50°C. to 180°C., preferably 60°C. to 120°C. The more suitably organic solvents are the common aromatic solvents such as benzene, toluene and the like. The compounds of the formula I may be isolated and recovered from the reaction mixture in which they are formed by working up by established procedures.

The compounds of the formulae II and III are each either known or may be prepared by the procedures available for the known compounds. The compounds of the formula II may be produced, for example, as described in U.S. Pat. No. 3,767,650 by employing the Vilsmeier Reaction involving the reaction of a compound of the formula IV:

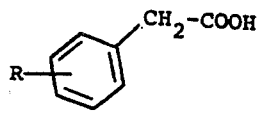

wherein R is as defined, with the disubstituted formamide reaction product obtained on reacting a compound of the formula V:

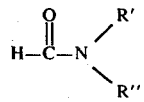

wherein R' amd R" are as defined, with a phosphorus oxyhalide, i.e., phosphorus oxychloride or phosphorus oxybromide.

Such preparation of the compounds is suitably carried out at elevated temperatures in the range of from 30°C. to 120°C., preferably 50°C. to 100°C., and preferably in the presence of an inert organic solvent which may be any of several conventional type organic solvents but which conveniently may be in whole or in part the formamide reacted with the phosphorus oxyhalide to obtain the disubstituted formamide reaction product. Thus, preferred solvents include dimethylformamide, diethylformamide and the like depending upon the particular compound of formula II being prepared. The reaction product of formula II may be recovered by working up of the reaction mixture in a conventional manner. The preparation of the disubstituted formamide reaction product is carried out in a conventional manner by reacting approximately equimolar amounts of the compound V and the phosphorus oxyhalide, preferably phosphorus oxychloride, at temperatures in the range of from 0°C. to 35°C., preferably 10°C. to 30°C.

Also, within the scope of the present invention are the pharmaceutically acceptable acid addition salts of the compounds of the formula I. Such salts include, by way of illustration, the hydrochloride, hydrosulfate, maleate and the like. Such salts may be prepared by conventional procedures and the free base forms may be also produced from the acid addition salt forms by conventional procedures.

The compounds of the formula I (and their pharmaceutically acceptable acid addition salts) are useful because they possess pharmacological activity in animals. In general, the compounds I effect a depression of the central nervous system and are useful as minor tranquillizers as indicated by a CNS depressant (docility) effect in behavior tests in mice (10–200 mg./kg.)

and/or by an inhibition of chemically induced seizures in mice on intraperitoneal administration (10–200 mg./kg.) using 50 mg./kg. of N-sulfamoylazepine to induce seizures. Certain of the compounds I represented by the compound of Example 1, in addition to the above indications, provide responses indicative of a spectrum of tranquillizer activity having a muscle relaxant component as indicated in the behavior test and by a neurological deficit and muscle relaxation in the "rotarod test" in mice on administration intraperitoneally (10–200 mg./kg.) essentially according to the method of Dunham et al., J. Am. Pharm. Assoc. 45:208, 1957.

The compound of the formula I are also useful as sleep-inducers as indicated by a reinduction of hexobarbital anesthesia in mice (10–200 mg./kg.) and by a potentiation of Thioridazine as determined by a loss of righting reflex according to the method of Reed-Muench, Am. J. Hygiene, 27:493–497 (1937), in which fasted but glucose maintained mice are administered 12.5 mg./kg. i.p. of Thioridazine followed immediately by the administration of graded doses totally from 10 to 150 mg./kg., i.p. of the test compound in a volume 0.1 ml./kg., of body weight, the mice being scored for loss of righting reflex 60 minutes after dosing.

For use of the compounds I as tranquilizers the effective dosage will vary depending upon known factors including the compound employed, mode of administration and the like. However, in general, satisfactory results are obtained when administered at a daily dosage of from 2 to 200 milligrams per kilograms, preferably given in divided doses 2 to 4 times a day or in sustained release form. For most mammals, the administration of from 140 to 2000 milligrams per day provides satisfactory results, and dosage forms suitable for internal administration comprise from about 35 to 1000 milligrams of the compound in admixture with a solid or liquid pharmaceutical carrier.

The sleep-inducing effective dosage of the compounds of the formula I will also vary depending upon known factors. However, in general, satisfactory results are obtained when the compounds are administered in a single dose at bedtime of from 2 to 200 milligrams per kilogram of body weight. For most mammals, the administration of a single dose of from 140 to 2000 milligrams provides satisfactory results and is typically administered at bedtime in admixture with a solid or liquid pharmaceutical carrier.

For the above usages, the compounds of the formula I are preferably combined with one or more conventional pharmaceutically acceptable carriers, and such other conventional adjuvants as may be desired or necessary, and the resulting composition administered orally in such forms as tablets, capsules, granules, dispersible powders, elixirs, syrups, suspensions and the like parenterally in the form of an injectable solution, suspension or the like, e.g., a sterile injectable aqueous suspension. Such compositions may be prepared according to any method known in the art for the manufacture of pharmaceutical compositions. In general, the compositions of the invention adapted for either oral or parenteral administration may contain 1% to 90% by weight of the active ingredient in combination with the inert carrier, more usually 3% to 40%.

The preferred mode of administration is oral administration and preferred pharmaceutical compositions from the standpoint of preparation and ease of administration are solid compositions, particularly hard-filled capsules and tablets.

A representative formulation for effecting tranquilization on administration four times a day is a capsule prepared by conventional techniques and containing the following ingredients:

| Ingredient | weight (mg.) |
| --- | --- |
| 1-(2-hydroxybutyl)-4-(m-trifluoromethylphenyl)-pyrazole | 100 |
| Lactose (finely divided) | 200 |

A representative capsule formulation prepared by conventional techniques and useful for effecting sleep induction at bedtime contains the following ingredients:

| Ingredient | Weight (mg.) |
| --- | --- |
| 1-(2-hydroxybutyl)-4-(m-trifluoromethylphenyl)-pyrazole | 150 |
| Lactose (finely divided) | 200 |

The generally preferred compounds of the invention from the standpoint of CNS depressant activity are further characterized by having R being hydrogen or R located at the m-position of the phenyl ring to which it is attached. It is usually more preferred to have R at said m-position and representing a substituent from the group of alkoxy, halo or trifluoromethyl, more preferably methoxy, fluoro, chloro and trifluoromethyl.

The following examples illustrate compounds of the invention and the manner of their preparation.

EXAMPLE 1

1-(2-hydroxybutyl)-4-(m-trifluoromethylphenyl) pyrazole

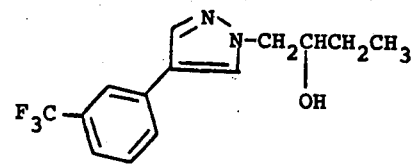

A mixture of 10 g. of 2-(m-trifluoromethylphenyl)-3-dimethylaminoacrolein; 5 g. of 2-hydroxybutylhydrazine and 100 ml. of benzene is refluxed for 2.5 hours. The benzene is evaporated off, ether added, and the reaction mixture cooled to obtain a precipitate which is recovered by filtering, washed with pentane, dissolved in methylene chloride, dried, treated with charcoal and filtered. The resulting solution is treated by addition of pentane and the resulting precipitate recovered by filtering, washed with pentane and dried under reduced pressure to obtain 1-(2-hydroxybutyl)-4-(m-trifluoromethylphenyl)-pyrazole, m.p. 77°–79°C.

EXAMPLE 2

Following the procedure of Example 1, the following additional compounds of the invention are prepared.
A. 1-(2-hydroxyethyl)-4-phenyl-pyrazole, m.p. 95°–98°C.
B. 1-(2-hydroxyethyl)-4-(p-methoxyphenyl)-pyrazole, m.p. 120°–125°C.
C. 1-(3-hydroxypropyl)-4-phenyl-pyrazole, m.p. 103°–106°C.

D. 1-(2-hydroxybutyl)-4-(m-methoxyphenyl)-pyrazole, m.p. 54°–56°C.
E. 1-(2-hydroxybutyl)-4-phenyl-pyrazole, m.p. 121°–123°C.
F. 1-(2-hydroxybutyl)-4-(m-fluorophenyl)pyrazole, m.p. 94°–96°C.

What is claimed is:
1. A compound of the formula:

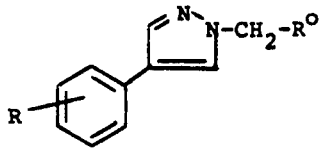

wherein
R° is hydroxyalkyl of 1 to 5 carbon atoms, and
R is hydrogen, fluoro, chloro, bromo, alkyl of 1 to 4 carbon atoms, alkoxy of 1 to 4 carbon atoms or trifluoromethyl,
or a pharmaceutically acceptable acid addition salt thereof.

2. A compound of claim 1 in which R° is of the formula:

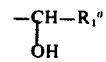

wherein $R_1°$ is straight chain alkyl of 1 to 4 carbon atoms.

3. A compound of claim 2 in which R° is of the formula:

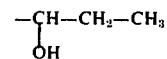

4. A compound of claim 1 in which R is selected from the group consisting of alkoxy, fluoro, chloro, bromo and trifluoromethyl.
5. A compound of claim 2 in which R is in the metaposition.
6. A compound of claim 5 in which R is trifluoromethyl.
7. The compound of claim 3 which is 1-(2-hydroxybutyl)-4-(m-trifluoromethylphenyl)-pyrazole.
8. The compound of claim 3 which is 1-(2-hydroxybutyl)-4-phenyl-pyrazole.
9. The compound of claim 3 which is 1-(2-hydroxybutyl)-4-(m-fluorophenyl)-pyrazole.
10. The compound of claim 3 which is 1-(2-hydroxybutyl)-4-(m-methoxyphenyl)-pyrazole.

* * * * *